United States Patent
Berggren

(10) Patent No.: US 10,060,935 B2
(45) Date of Patent: *Aug. 28, 2018

(54) APOIII AND THE TREATMENT AND DIAGNOSIS OF DIABETES

(71) Applicant: BioCrine AB, Solna (SE)

(72) Inventor: Per-Olof Berggren, Solna (SE)

(73) Assignee: BioCrine AB, Solna (SE)

( * ) Notice: Subject to any disclaimer, the term of this patent is extended or adjusted under 35 U.S.C. 154(b) by 0 days.

This patent is subject to a terminal disclaimer.

(21) Appl. No.: 15/409,027

(22) Filed: Jan. 18, 2017

(65) Prior Publication Data

US 2017/0138968 A1 May 18, 2017

Related U.S. Application Data

(60) Continuation of application No. 14/867,523, filed on Sep. 28, 2015, now abandoned, which is a continuation of application No. 14/222,058, filed on Mar. 21, 2014, now Pat. No. 9,169,484, which is a continuation of application No. 13/935,825, filed on Jul. 5, 2013, now Pat. No. 8,716,241, which is a continuation of application No. 13/105,559, filed on May 11, 2011, now Pat. No. 8,507,444, which is a continuation of application No. 12/196,536, filed on Aug. 22, 2008, now Pat. No. 8,030,288, which is a division of application No. 10/834,525, filed on Apr. 29, 2004, now Pat. No. 9,062,306.

(60) Provisional application No. 60/466,517, filed on Apr. 29, 2003.

(51) Int. Cl.
| | |
|---|---|
| *C12N 15/113* | (2010.01) |
| *G01N 33/92* | (2006.01) |
| *G01N 33/50* | (2006.01) |
| *C07K 16/18* | (2006.01) |

(52) U.S. Cl.
CPC ............ *G01N 33/92* (2013.01); *C07K 16/18* (2013.01); *G01N 33/507* (2013.01); *G01N 33/5041* (2013.01); *C07K 2317/76* (2013.01); *G01N 2333/775* (2013.01); *G01N 2440/38* (2013.01); *G01N 2800/042* (2013.01); *G01N 2800/50* (2013.01)

(58) Field of Classification Search
CPC .............................. C12N 15/113; C07K 16/00
See application file for complete search history.

(56) References Cited

U.S. PATENT DOCUMENTS

| 6,506,559 | B1 | 1/2003 | Fire et al. |
|---|---|---|---|
| 7,598,227 | B2 | 10/2009 | Crooke et al. |
| 8,030,288 | B2 | 10/2011 | Berggren |
| 8,084,439 | B2 | 12/2011 | Berggren |
| 8,507,444 | B2 | 8/2013 | Berggren |
| 8,716,241 | B2 | 5/2014 | Berggren |
| 9,169,484 | B2 | 10/2015 | Berggren |
| 2002/0161187 | A1* | 10/2002 | Jackowski ......... G01N 33/6893 530/327 |
| 2004/0224304 | A1 | 11/2004 | Berggren et al. |
| 2009/0061475 | A1 | 3/2009 | Berggren et al. |
| 2009/0081201 | A1 | 3/2009 | Berggren et al. |

FOREIGN PATENT DOCUMENTS

| WO | 2003/020765 | 3/2003 |
|---|---|---|
| WO | 2004/093783 | 4/2004 |

OTHER PUBLICATIONS

Takahashi et al. Metabolism 52:1354-1359 (Year: 2003).*
Efendic, (1991) J Intern Med Suppl 735, 9-22.
Juntti-Berggren, P. O. (1993) Science 261, 86-90.
Hellman, B. (1965) Ann N Y Acad Sci 131, 541-58.
Nilsson, T., (1987) Biochem J 248, 329-36.
Lernmark, A. (1974) Diabetologia 10, 431-8.
Bengtsson-Olivecrona, G. (1991) Methods Enzymol 197, 345-56.
Kindmark, (1992) FEBS Lett 303, 85-90.
Fredenrich, A. (1998) Diabetes Metab 24, 490-5.
Krauss, R. M., Herbert, P. N., Levy, R. I. & Fredrickson, D. S. (1973) Circ Res 33, 403-11.
Ginsberg, H. N., (1986) J Clin Invest 78, 1287-95.
Kowal, R. C., (1990) J Biol Chem 265, 10771-9.
Maeda, N., (1994) J Biol Chem 269, 23610-6.
Ito, Y., A (1990) Science 249, 790-3.
Brewer, H. B., (1974) J Biol Chem 249, 4975-84.
Kashyap, M. L., (1981) J Lipid Res 22, 800-10.
Roghani, A. & Zannis, V. I. (1988) J Biol Chem 263, 17925-32.
Chen, M., (1994) J Lipid Res 35, 1918-24.
Reaven, G. M., (1994) J Lipid Res 35, 820-4.

(Continued)

*Primary Examiner* — Brian A Whiteman

(74) *Attorney, Agent, or Firm* — McDonnell Boehnen Hulbert & Berghoff LLP

(57) ABSTRACT

The present invention provides methods of identifying candidate compounds for the treatment of type I diabetes comprising contacting pancreatic β cells with an amount of apolipoprotein CIII ("apoCIII") effective to increase intracellular calcium concentration, in the presence of one or more test compounds, and identifying those test compounds that inhibit an apoCIII-induced increase in intracellular calcium concentration in the pancreatic β cells. The present invention also provides methods for treating patients with type I diabetes comprising administering to the patient an amount effective of an inhibitor of apoCIII to reduce apoCIII-induced increase in intracellular calcium concentration in pancreatic β cells.

5 Claims, 4 Drawing Sheets

Specification includes a Sequence Listing.

(56) References Cited

OTHER PUBLICATIONS

Briones, E. R., (1984) Metabolism 33, 42-9.
Joven, J., (1989) Clin Chem 35, 813-6.
Stewart, M. W., (1994) J Intern Med Suppl 736, 41-6.
Bren, N. D., (1993) Mayo Clin Proc 68, 657-64.
Nestel, P. J. & Fidge, N. H. (1982) Adv Lipid Res 19, 55-83.
Blackett, P., (1988) South Med J 81, 469-73.
al Muhtaseb, N., (1992) Pediatrics 89, 936-41.
Manzato, E., Z (1993) Diabetes Care 16, 469-75.
Reverter, J. L., (1993) Clin Chim Acta 223, 113-20.
O'Looney, P., (1985) J Biol Chem 260, 428-32.
Callow, M. J. & Redgrave, T. G. (1993) Biochim Biophys Acta 1168, 271-9.
Bar-On, H., Roheim, P. S. & Eder, H. A. (1976) J Clin Invest 57, 714-21.
Ito, Y., Breslow, J. L. & Chait, B. T. (1989) J Lipid Res 30, 1781-7.
Cejvan et al., (2003), Diabetes, 52, 1176-1181.
Zambre et al., (1999), Biochem. Pharmacol., 57, 1159-1164.
Fagan et al., (1998), Surgery, 124, 254-259.
Kohler and Milstein, (1975), Nature, 256, 495-497.
Jones, et al., (1986), Nature, 321, 522-525.
Morrison et al., (1984), Proc. Natl. Acad. Sci., U.S.A., 81, 6851-6855.
Morrison and Oi, (1988), Adv. Immunol, 44, 65-92.
Verhoeyer et al., (1988), Science, 239, 1534-1536.
Padlan, (1991), Molec. Immun., 28, 489-498.
Kettleborough, C.A. et al., (1991), Protein Eng., 4(7), 773-783.
Alaupovic, P., et al., (1988), Clin. Chem., vol. 34, pp. B13-B27.
Davignon, J., et al., (1998), Canadian Journal of Cardiology, vol. 14 Suppl B, pp. 28B-38B.
Alsayed, N., et al., (1988), Clinical Chemistry, vol. 34(1), pp. 49-52.
Perez, A., et al., (200), Archives of Internal Medicine, vol. 160(18), pp. 2756-2762.
Tada, N., et al., (1983), The Tohoku Journal of Experimental Medicine, vol. 141 Suppl, pp. 619-626.
Rabinovitch, A., et al., (2001), Endocrinology, vol. 142(8), pp. 3649-3655.
Junti-Beggren, Lisa, et al., (2004), Proceedings of the National Academy of Sciences of the United Stats of America, vol. 101(27), pp. 10090-10094.
Dekki, N., et al. (2007), Biosci. Rep., vol. 27:321-326.
Morgan, et al., (2007) "Serum protein oxidation and apolipoportein CIII levels in people with systemic lupus erythematosis with and without nephristis," Free Radic Res, 41(12):1301-12.
Onat, et al., (2003) "Apoliproprtein C-III, a strong discriminant of coronary risk in men and a determinant of the metabolic syndrome in both genders," Atherosclerosis, 168(1):81-9.
Juntti-Begrren (2003) "Apolipoportein CIII leads to Ca2+-dependent beta-cell death in type 1 diabetes," Poster presentation, Stockholm Nov. 2003, 13P.
Storling, et al., (2011) "apolipoprotein CIII reduces proinflammatory cytokine-induced apoptosis in rat pancreatic islets via the AKT prosurvival pathway," Endocrinology, 152(8):3040-3048.
National Diabetes Fact Sheet, 2003.
BPAI decision U.S. Appl. No. 10/834,525 dated Feb. 12, 2015, pp. 1-9.
Klein et al. Arterioscler Thromb Vase Bioi. 22; a-50, p. 284, 2002.
Tas et al., The Lancet, 1994, vol. 343, pp. 1194-1195.

* cited by examiner

SEQUENCE LISTING

```
<160> NUMBER OF SEQ ID NOS: 8

<210> SEQ ID NO 1
<211> LENGTH: 487
<212> TYPE: DNA
<213> ORGANISM: Homo sapiens
<220> FEATURE:
<221> NAME/KEY: CDS
<222> LOCATION: (1)..(300)

<400> SEQUENCE: 1
```

```
atg cag ccc cgg gta ctc ctt gtt gtt gcc ctc ctg gcg ctc ctg gcc      48
Met Gln Pro Arg Val Leu Leu Val Val Ala Leu Leu Ala Leu Leu Ala
1               5                   10                  15 tct gcc cga gct tca gag gcc gag gat gcc tcc ctt ctc agc ttc atg      96
Ser Ala Arg Ala Ser Glu Ala Glu Asp Ala Ser Leu Leu Ser Phe Met
            20                  25                  30 cag ggt tac atg aag cac gcc acc aag acc gcc aag gat gca ctg agc     144
Gln Gly Tyr Met Lys His Ala Thr Lys Thr Ala Lys Asp Ala Leu Ser
        35                  40                  45 agc gtg cag gag tcc cag gtg gcc cag cag gcc agg ggc tgg gtg acc     192
Ser Val Gln Glu Ser Gln Val Ala Gln Gln Ala Arg Gly Trp Val Thr
    50                  55                  60 gat ggc ttc agt tcc ctg aaa gac tac tgg agc acc gtt aag gac aag     240
Asp Gly Phe Ser Ser Leu Lys Asp Tyr Trp Ser Thr Val Lys Asp Lys
65                  70                  75                  80 ttc tct gag ttc tgg gat ttg gac cct gag gtc aga cca act tca gcc     288
Phe Ser Glu Phe Trp Asp Leu Asp Pro Glu Val Arg Pro Thr Ser Ala
                85                  90                  95 gtg gct gcc tga gacctcaata ccccaagtcc acctgcctat ccatcctgcc         340
Val Ala Ala agctccttgg gtcctgcaat ctccagggct gccctgtag gttgcttaaa agggacagta     400
ttctcagtgc tctcctaccc cacctcatgc ctggcccccc tccaggcatg ctggcctccc    460
aataaagctg gacaagaagc tgctatg                                       487

<210> SEQ ID NO 2
<211> LENGTH: 99
<212> TYPE: PRT
<213> ORGANISM: Homo sapiens

<400> SEQUENCE: 2

Met Gln Pro Arg Val Leu Leu Val Val Ala Leu Leu Ala Leu Leu Ala
1               5                   10                  15

Ser Ala Arg Ala Ser Glu Ala Glu Asp Ala Ser Leu Leu Ser Phe Met
            20                  25                  30

Gln Gly Tyr Met Lys His Ala Thr Lys Thr Ala Lys Asp Ala Leu Ser
        35                  40                  45

Ser Val Gln Glu Ser Gln Val Ala Gln Gln Ala Arg Gly Trp Val Thr
    50                  55                  60

Asp Gly Phe Ser Ser Leu Lys Asp Tyr Trp Ser Thr Val Lys Asp Lys
65                  70                  75                  80

Phe Ser Glu Phe Trp Asp Leu Asp Pro Glu Val Arg Pro Thr Ser Ala
                85                  90                  95

Val Ala Ala

<210> SEQ ID NO 3
<211> LENGTH: 2509
<212> TYPE: DNA
<213> ORGANISM: Rattus norvegicus

<400> SEQUENCE: 3
taaagagacg gatgacctac agccccaggc ccacccattc aacaggccta gctcattccc     60
aagcccagac atcaaggcat gggacaccca cgcatggcag cttcgtgtcc agctttatta    120
gggacagcat gtttaggtga ggtctgggga gggataaagg catgagaata ctttccccc     180 ttagagcaac cttcggaggc agcaggatag atgccagac acatctggaa catggaggtc    240
tcacggctca agagttggtg ttgttagttg gtcctcaggg ccagactccc agaggccagt    300
```

```
gaacttatca gtgaacttgc tccagtagcc tttcagggat ttgaagcgat tgtccatcca      360
gcccctgggg gttaaaacag taataggtgt gtgtgtgtgt gtgtgtgtgt gtgtgtgtgt      420
gtgtgtgtgt gtgtgtgtgt gaaaagatct cctgtgggca gctagaccca ggggtgcacc      480
taggcctcca ctggctccct aagccaccag caccaccta cctagcacca ccctcagaat       540
cacctgcagc taccactcaa ggtggaggag atggtaaagg ctaagaaaac ccaccttcat      600
cagagcccca ttacctcccg tccaatctct cttcaggcct gaggcaccaa ccactgggga      660
ggtggatact aaggtcagct tgcctttgta gtccatagaa acagtgtcct tgaggtgtcc      720
catccctggc tctaagtgga tggatcaagg gaggggtgaa ctttctgttt ggaaacatta     780
ccagagggct tctaagctct gtgatctagg ccaggttatc taactctttc ccagctgcgg      840
aggtagatag tacctctcca caacctgttc tgggcacaga gactgtcaac atcttttgct      900
acataggcaa tgatcaaatg tcacgtaaac gattggcagg gtaatgtttc atcacgggca      960
agatgcctca cttaggttga gcccagggat ggaaacaggg cagaaccccc aacccgtaat     1020
gctcaacctt ccaacttccc tgtaatcaga gcaggaaggc ctcccagagc acccctaga     1080 ccctgtgctc aaagaagaaa acctgcaggg aggctgaacg ctcctcaggc tgctctgagg      1140
agaagcagag gagatagaag aagtctgctt gcactgcctg tcatcttagt cacagtcccc      1200
agcaaaggcc ccgtgagaga ctggatgctc agacgggccc aagaccctgg taaacttggt      1260
gggccacagt ctccgtgtcc agggcctcag caccagggca ggaggggcga ggaccaggaa      1320
aggaggtccg tgtgcatacc tggccaccac agctatatca gactcctgca tgctgcttag      1380
tgcatcctgg accgtcttgg aggcttgttc catgtagccc tgcatagagc ccagcagcaa      1440
ggatccctct ccctcatcag ctcctgcaag agagcagagt tgagccaggc cagccctcag      1500
ctcttgccca gccatcgctt ttcagggtag ggtcccagga ccagctcccg cagaaatccc      1560
agccccactt ccaccagctt acgggcagag gccaggagag ccacgagggc cacgatgagg      1620
agcattcggg gctgcatggc acctgtgcac ctgcgggaga ccatcttgtg agagggtatt      1680
gtggatctcc acatctaagc ccttccctgg agaacaccac ggcccctctg tcatgaatcc      1740
ccaagccttt ctcctactga tatcagctct cggagagaga actaagaaga cccagaccca      1800
ccccaagggg ctggaaggtg gaatgtggga atcctctgca aagcagaaca tctacccagc      1860
ctctgcccca atatatggag aaacaacagg tttcttttc tctctaggct tcaggctttt       1920
cagtctgggg taggcacgga tatcaaaggc ttctaatagc tcagagcaag acgaacaagg      1980
ggcagcatga cccagttccc aatcagctct gccactaccc agtgcaaggc ttttttgccc     2040
agtggcctcc cttcctcag cttctagcct cccccaccca ccaggatacc caagggctgg      2100
aggccgtgaa ttccaagcat tctgtaggct agctggctga gtggccagag cgtcttctct     2160
ctgtctcctc cctccttcc tctcctcccc aggggcatta cctggagtag ctagctgctt       2220
ctagggataa aactgggcag gcaagccggg acgctctgat ctgttttata ttggctccag     2280
gatgggacag cgggcacaga aggcccagtg agctggtcaa aggtcacctg ctgaacagtc      2340
cagaccagag cccgaggcag ggaggccatg cagccagctg ccagaggagt tgagaaatcc      2400
ctcagagatt gccacaccg ttcacttcca cctccgcagc caagagatca gctactgacc       2460
tgcctcgatg agactggtga gacaggaaaa gactcagggg acaagcctt                 2509
```

<210> SEQ ID NO 4
<211> LENGTH: 101
<212> TYPE: PRT
<213> ORGANISM: Rattus norvegicus

<400> SEQUENCE: 4

| | | | | | | | | | | | | | | | |
|---|---|---|---|---|---|---|---|---|---|---|---|---|---|---|---|
| Met | Gln | Pro | Arg | Met | Leu | Leu | Ile | Val | Ala | Leu | Val | Ala | Leu | Leu | Ala |
| 1 | | | | 5 | | | | | 10 | | | | | 15 | |
| Ser | Ala | Arg | Ala | Asp | Glu | Gly | Glu | Gly | Ser | Leu | Leu | Leu | Gly | Ser | Met |
| | | | 20 | | | | | 25 | | | | | 30 | | |
| Gln | Gly | Tyr | Met | Glu | Gln | Ala | Ser | Lys | Thr | Val | Gln | Asp | Ala | Leu | Ser |
| | | | 35 | | | | | 40 | | | | | 45 | | |
| Ser | Met | Gln | Glu | Ser | Asp | Ile | Ala | Val | Val | Ala | Ser | Arg | Gly | Trp | Met |
| | 50 | | | | | 55 | | | | | 60 | | | | |
| Asp | Asn | Arg | Phe | Lys | Ser | Leu | Lys | Gly | Tyr | Trp | Ser | Lys | Phe | Thr | Asp |
| 65 | | | | | 70 | | | | | 75 | | | | | 80 |
| Lys | Phe | Thr | Gly | Leu | Trp | Glu | Ser | Gly | Pro | Glu | Asp | Gln | Leu | Thr | Thr |
| | | | | 85 | | | | | 90 | | | | | 95 | |
| Pro | Thr | Leu | Glu | Pro | | | | | | | | | | | |
| | | | 100 | | | | | | | | | | | | |

<210> SEQ ID NO 5
<211> LENGTH: 3262
<212> TYPE: DNA
<213> ORGANISM: Macaca fascicularis
<220> FEATURE:
<221> NAME/KEY: CDS
<222> LOCATION: (858)..(912)
<220> FEATURE:
<221> NAME/KEY: CDS
<222> LOCATION: (1048)..(1171)
<220> FEATURE:
<221> NAME/KEY: CDS
<222> LOCATION: (2871)..(2988)

<400> SEQUENCE: 5

| | |
|---|---|
| ctgcagggct ggcgggacag cagcatggac acagtctcct ggggatttcc caactctccc | 60 |
| gccagcttgc tgcctctggc cgccctgcct caggccctgg tctctgatca gcaggtgacc | 120 |
| tttgcccagt gccctgggtc ctcagtgcct gctgccctgg agacaatata aaacaggctc | 180 |
| agaaccctcc tgcctgcctg ctctgttcat ccctagaggc agctgctcca ggtaatgccc | 240 |
| tctggggagg ggaaagagga ggggaggagg atgaagagga gcaagaggag ctccctgccc | 300 |
| agcccagcca gcaagcctgg agaaacactt gctagagcta aggaagcctc ggagctggac | 360 |
| gggtgccccc aaccctcat cataacctga agaaaatgga ggcccgggag gggtgtcact | 420 |
| tgcccaaagc tacacagggg gtggggctgg aaatggttcc aagtgcaggc ttccccgtca | 480 |
| ttctgcaggc ttagggctgg aggaagcctt agacagccca gtcctaccca gacagggaaa | 540 |
| ctgaggcctg gagagggcca gaaagcccca agtcacaca gcatgttggc tgcactggac | 600 |
| agagaccagt ccagaccgca ggtgccttga tgtccagtct ggtgggtttt ctgctccatc | 660 |
| ccacctacct cccttttgggc ccctcactag tccccttctg agagcccgta ttagcaggaa | 720 |
| gcaggccccc actccctctg gcagaccgag ctcaggtccc accttagggg ccatgccacc | 780 |
| tgtccaggga ggggtccaga ggcatggggg cctggggtgc ccctcacagg acaattcctt | 840 |

| | |
|---|---|
| gcaggaacag aggcgcc atg cag ccc cgg gta ctc ctt gtt gct gcc ctg | 890 |
|                                      Met Gln Pro Arg Val Leu Leu Val Ala Ala Leu | |
|                                      1               5                    10 | |
| ctg tca ctc ctg gcc tct gcc a gtaagcactt ggtgggactg ggctgggggc | 942 |
| Leu Ser Leu Leu Ala Ser Ala | |
|                15 | |
| aggatggagg tggcttgggg atcccagtcc taatgggtgg tcaagcagga gctcagggct | 1002 |

```
cgcctagagg ccgatccacc actctcagcc ctgctctttc ctcag ga gct tca gag      1058
                                                  Arg Ala Ser Glu
                                                       20 gcc gag gac acc tcc ctt ctt ggc ttc atg cag ggc tac atg cag cat       1106
Ala Glu Asp Thr Ser Leu Leu Gly Phe Met Gln Gly Tyr Met Gln His
         25                  30                  35 gcc acc aag acc gcc aag gat gca ctg acc agc gtc cag gag tcc cag       1154
Ala Thr Lys Thr Ala Lys Asp Ala Leu Thr Ser Val Gln Glu Ser Gln
     40                  45                  50 gtg gcc cag cag gcc ag gtacaccgc tggcctccct ccccatccct                1201
Val Ala Gln Gln Ala Arg
 55              60 catgccagct ccctccattc ccacccgccc tgccctggtg agatcccagc aatggaatgg     1261
aggtgccagc ctccctggt cctgtgcctc tttggcctcc tctttcctca cagggccttg      1321
gtcaggctgc tgtgggagag acgacagagt tgagactgcg ttcccccgg tccctcctt       1381 tctcccagag cagttctagg gtgggccatt ttagccctca tttccatttt cctttccttt     1441
tctttctttt tcttttcttt tttttctttt ctttctttt tttttttgag atggagtctc      1501
cctctgtcac ccaggctaga gtgcagtggt gcgatctcag cggatctcgg ctcactgcaa     1561
cctctgcctc ccaggttcac cccattctcc tgcctcagcc tcccaagtag ctgggattac     1621
aggcgtgcca ccacatccag ctactttttg tattttctc agagacgggg tttccccatg      1681
ttggacaggc tggtcttgaa ctcctgacct caggtgatct gcctacctcg gcctcccaaa     1741
ttgctgggat tacaggcatg agccactgcg cctgacccca ttttccttttt ctgaaggtct    1801 ggctagagca gaggtcctca accttttgg caccagggac cagttttgtg gtagacagtt      1861
tttccatggg tcagcgggga tggcttgggg atgaaactgc tccacctcag atcaccaggc     1921
attggattct cctaagaagc cctccacccc gaccctggc atgcgcagtt cacaacaggt      1981
ttcacactcc tgtgagaatc taatgccgcc taacctgaca gaaggcgggg cttgggcggt     2041
attcctctgt cacccatcac tcactttgtg ctgtgcagcc tggctcctaa ctggccatgg     2101
accagtaccc atctgtgact gggggctgg gaccctgg gctaggggtt tgccttggga        2161 ggcccacct ggcccaattc tagcctgggt atgagagtgc ttctgctttg ttccaagacc      2221
tggggccagg gtgagtagaa gtgtgtcctt cctctcccat cctgcccctg ccatcggtc      2281 ctctcctctc cctactccct tccccacctc accctgactg gcattggctg gcatagcaga    2341
ggttgtttat aagcattctt aatcctcaga accggctttg gggtaggtgt tattttccca    2401
ctttgcagat gagaaaattg aggctcagag cgattaggtg acctgcccca gatcacacaa    2461
ctaatcaatc ctccaatgac tttccaaatg agaggtcgcc tccctctgtc ctaccctgct    2521
cggaaccacc aggatataca actccagggg atactgtctg cacagaaaac aatgacagcc    2581
ttgacctttc acatctcccc accctgtcac tctgtgcctc aagcccaggg gcaaaaacat    2641
ctgaggtcac ctggagacgg cagggttcga cttgtgctgg ggttcctgta agggcatctc    2701
ttctcccagg gtggcagctg tgggcagtcc tgcctgaggt ctcagggctg ttgtccagtg    2761
aagttgagag ggtggcaggg agagccagtg gggacatggg tgtgggtccc atagttgcct    2821
ccaaaggagt tctcatgccc tgctctgttg cttcccctta ctgatttag a ggc tgg      2877
                                                         Gly Trp gtg acc gat ggc ttc agt tcc ctg aaa gac tac tgg agc acc gtt aag      2925
Val Thr Asp Gly Phe Ser Ser Leu Lys Asp Tyr Trp Ser Thr Val Lys
             65                  70                  75 gac aag tta tct ggg ttc tgg gat ttg aac cct gag gcc aaa ccc act      2973
Asp Lys Leu Ser Gly Phe Trp Asp Leu Asn Pro Glu Ala Lys Pro Thr
```

```
ctg gct gag gct gcc tgagacctca ataccccaag tccacctgcc tgtccatcct      3028
Leu Ala Glu Ala Ala
 95 gccagctcct tgggtcctgc agcctccagg gctgccctg taggttgctt aaaagggaca     3088 gtattctcag tgccctccta ccgcacctca tgcctggccc cctccaggc agggtgtcct     3148 cccaataaag ctggacaaga agctgctatg agtgggccgt cacaagtgtg ccatctgtgt    3208 ctgggtatgg gaaagggtcc gaggctgttc tgtgggtagg cactggacga ctgc          3262
```

<210> SEQ ID NO 6
<211> LENGTH: 99
<212> TYPE: PRT
<213> ORGANISM: Macaca fascicularis

<400> SEQUENCE: 6

```
Met Gln Pro Arg Val Leu Leu Val Ala Ala Leu Leu Ser Leu Leu Ala
 1               5                  10                  15

Ser Ala Arg Ala Ser Glu Ala Glu Asp Thr Ser Leu Leu Gly Phe Met
             20                  25                  30

Gln Gly Tyr Met Gln His Ala Thr Lys Thr Ala Lys Asp Ala Leu Thr
         35                  40                  45

Ser Val Gln Glu Ser Gln Val Ala Gln Gln Ala Arg Gly Trp Val Thr
     50                  55                  60

Asp Gly Phe Ser Ser Leu Lys Asp Tyr Trp Ser Thr Val Lys Asp Lys
 65                  70                  75                  80

Leu Ser Gly Phe Trp Asp Leu Asn Pro Glu Ala Lys Pro Thr Leu Ala
                 85                  90                  95

Glu Ala Ala
```

<210> SEQ ID NO 7
<211> LENGTH: 2411
<212> TYPE: DNA
<213> ORGANISM: Mus musculus
<220> FEATURE:
<221> NAME/KEY: CDS
<222> LOCATION: (54)..(350)

<400> SEQUENCE: 7

```
gctacatcag ggctgtgca gcgtcgccca tactccgagc aaagaactgt ggc cag         56
                                                         Gln
                                                          1 agg cag tcg agg tta gtg agg act gcg agg cag aca ctt tgc tgt gtt      104
Arg Gln Ser Arg Leu Val Arg Thr Ala Arg Gln Thr Leu Cys Cys Val
         5                  10                  15 caa atc caa gtc aag ggt aca aaa atg cag agc aat aaa gcc ttt aac      152
Gln Ile Gln Val Lys Gly Thr Lys Met Gln Ser Asn Lys Ala Phe Asn
     20                  25                  30 ttg gag aag cag aat cat act cca agg aag cat cat cag cat cac cac      200
Leu Glu Lys Gln Asn His Thr Pro Arg Lys His His Gln His His His
 35                  40                  45 cag cag cac cat cag cag caa cag cag cag cag caa cag cca ccc          248
Gln Gln His His Gln Gln Gln Gln Gln Gln Gln Gln Pro Pro
 50                  55                  60                  65 cca cca ata cct gca aat ggc cag cag gcc agc agc cag aat gaa ggc      296
Pro Pro Ile Pro Ala Asn Gly Gln Gln Ala Ser Ser Gln Asn Glu Gly
             70                  75                  80 ttg act att gac ctg aag aat ttt agg aaa cca gga gag aag acc ttt      344
Leu Thr Ile Asp Leu Lys Asn Phe Arg Lys Pro Gly Glu Lys Thr Phe
```

|  | 85 | 90 | 95 |  |
|---|---|---|---|---|
| aca cag cgtagccgtc tctttgtggg caatcttccc cctgatatca ctgaggagga | | | | 400 |
| Thr Gln | | | | |
| aatgaggaaa ctatttgaga aatatggaaa agcaggcgaa gttttcattc ataaggataa | | | | 460 |
| aggctttggc tttattcgct tggaaacacg aaccctagcg gaaattgtca aagtggagct | | | | 520 |
| ggacaacatg cccctccgtg ggaagcagct gcgagtgcgc ttcgcctgtc acagtgcatc | | | | 580 |
| ccttacagtc cgcaaccttc ctcagtacgt gtcgaacgaa ctgctggaag aagcttttc | | | | 640 |
| tgtgttcggc caggtggaga gggctgtagt cattgtggat gaccgaggaa ggccctcagg | | | | 700 |
| gaaaggcatt gttgagttct cagggaagcc agctgctcgg aaagctctgg acagatgcag | | | | 760 |
| tgaaggctcc ttcttgctga ctacatttcc ttggcctgtg actgtggagc ctatggacca | | | | 820 |
| gttagatgat gaagagggac ttccagagaa actggttata aaaaaccagc aattccacaa | | | | 880 |
| ggagagagaa cagccaccca gatttgcaca acctggctcc tttgagtatg agtatgccat | | | | 940 |
| gcgctggaag gcactcattg agatggaaa gcaacagcag gatcaagtgg atcggaacat | | | | 1000 |
| caaggaggct cgtgagaagc tggagatgga gatggaggct gcacgtcatg agcaccaggt | | | | 1060 |
| tatgctaatg aggcaggatt tgatgagacg tcaagaagag cttcggagaa tggaggagct | | | | 1120 |
| gcataaccaa gaggttcaga agcgaaagca gttagaactc aggcaggaag aggaacgcag | | | | 1180 |
| gcgccgtgag aagagatgc ggcgacaaca agaggaaatg atgcgccgac agcaggaagg | | | | 1240 |
| attcaaggga accttccctg atgcgagaga acaagagata cggatgggcc aaatggctat | | | | 1300 |
| gggaggtgct atgggcataa acaatagagg cgcgatgccc cctgctcctg tgccacctgg | | | | 1360 |
| tactccagct cctccaggac ctgccactat gatgccagat ggaacccttg gattgacccc | | | | 1420 |
| accaacaact gaacgttttg gccaagctgc aacaatggaa ggaattggag caattggtgg | | | | 1480 |
| aactcctcct gcattcaacc gtccagctcc gggagctgaa tttgctccaa ataaacgccg | | | | 1540 |
| ccgatattag ataaagttgc attgtctagt ttcctgcagc ccttaaaaga agggccctt | | | | 1600 |
| ttggactagc cagaattcta ccctggaaaa gtgttagggg ttcttcccaa tagataggcc | | | | 1660 |
| ttccctgctt gtactactct agggatcatg cttgaagtca gagggcagga aaggggtgg | | | | 1720 |
| tattcaacaa gtcaaagtct gtggtatatt gctttatcaa gactgtctgg tgcattcctg | | | | 1780 |
| aactatatta attgttgagg gcctggagaa ccatgggaaa atgaactcag agctccatta | | | | 1840 |
| atcttgatca ttccttctct ctctttctct ctctcttgtt ttaattactt tctcatcttt | | | | 1900 |
| attcccctca acccctgaga cactgccata tataccacaa accataaaca tcctccaatg | | | | 1960 |
| acctagcccc atccctccat tcactcccag gtaagaattc agacaaatgt ccacagaggt | | | | 2020 |
| tacagcatac gtacggttgt gttatatctc atatatgacc ccttcatgtc ctaaggaaga | | | | 2080 |
| cattttctct tagaggtttt cattttagta tatcttaaaa gaatcttgtg ttaccttgcc | | | | 2140 |
| tccatctttt tcttgggtaa ggactacact ttgtgtctct gatgttgctg ttcacagctt | | | | 2200 |
| ttcttgatag gcctagtaca atcttgggaa caggttgct gtgtggtgaa ggtctgacag | | | | 2260 |
| tagttcttag tcttgcctat cttaggtagc tacgctgtgc atttttattg gtatactatg | | | | 2320 |
| aattgttcca gataccttca gtttggaaag ttttctgaga aatggagacg tcatgcggca | | | | 2380 |
| tcaccttatt aaaatgcatt tgaagccttt t | | | | 2411 |

<210> SEQ ID NO 8
<211> LENGTH: 99
<212> TYPE: PRT
<213> ORGANISM: Mus musculus

```
<400> SEQUENCE: 8

Gln Arg Gln Ser Arg Leu Val Arg Thr Ala Arg Gln Thr Leu Cys Cys
1               5                   10                  15

Val Gln Ile Gln Val Lys Gly Thr Lys Met Gln Ser Asn Lys Ala Phe
            20                  25                  30

Asn Leu Glu Lys Gln Asn His Thr Pro Arg Lys His His Gln His His
        35                  40                  45

His Gln Gln His His Gln Gln Gln Gln Gln Gln Gln Gln Gln Gln Pro
        50                  55                  60

Pro Pro Pro Ile Pro Ala Asn Gly Gln Gln Ala Ser Ser Gln Asn Glu
65                  70                  75                  80

Gly Leu Thr Ile Asp Leu Lys Asn Phe Arg Lys Pro Gly Glu Lys Thr
                85                  90                  95

Phe Thr Gln
```

APOIII AND THE TREATMENT AND DIAGNOSIS OF DIABETES

CROSS REFERENCE

This application is a Continuation of U.S. application Ser. No. 14/867,523 filed on Sep. 28, 2015, which is a Continuation of U.S. application Ser. No. 14/222,058 filed on Mar. 21, 2014, which is a Continuation of U.S. application Ser. No. 13/935,825, filed Jul. 5, 2013, now U.S. Pat. No. 8,716,241 issues May 6, 2014, which is a Continuation of U.S. application Ser. No. 13/105,559, filed May 11, 2011, now U.S. Pat. No. 8,507,444 issued Aug. 13, 2013, which is a Continuation of U.S. application Ser. No. 12/196,536, filed: Aug. 22, 2008, now U.S. Pat. No. 8,030,288, issued Oct. 4, 2011, which is a Divisional of U.S. application Ser. No. 10/834,525, filed Apr. 29, 2004, now U.S. Pat. No. 9,062,306 issues Jun. 23, 2015, which claims priority of U.S. Provisional Patent Application 60/466,517 filed Apr. 29, 2003, all incorporated by reference herein in their entirety.

BACKGROUND OF THE INVENTION

Voltage-gated L-type $Ca^{2+}$-channels have an important physiological role in pancreatic β-cell ("β-cell") signal-transduction (1). These channels constitute an essential link between transient changes in membrane potential and insulin release from β-cells. Changes in cytoplasmic free $Ca^{2+}$ concentration ($[Ca^{2+}]_i$) in the β-cell are associated with the activation of a spectrum of intracellular signals and are strictly regulated, as prolonged high $[Ca^{2+}]_i$ is harmful to the cells.

In type 1 diabetes (T1D), there is a specific destruction of the insulin secreting pancreatic β-cell. Sera from newly diagnosed type 1 diabetic (T1D) patients have been shown to increase the activity of voltage-gated L-type $Ca^{2+}$-channels in β-cells resulting in increased $[Ca^{2+}]_i$ upon depolarization and β-cell apoptosis, effects that can be prevented by $Ca^{2+}$-channel blockers (2). However, it has not been determined what factor in T1D serum is responsible for the changes in $[Ca^{2+}]_i$.

We now demonstrate that apolipoprotein CIII (apoCIII) is increased in serum from T1D patients and that this serum factor both induces increased cytoplasmic free $Ca^{2+}$ concentration ($[Ca^{2+}]_i$) and β-cell death.

SUMMARY OF THE INVENTION

In one aspect, the present invention provides methods of identifying candidate compounds for the treatment of type I diabetes comprising contacting pancreatic β cells with an amount of apolipoprotein CIII ("apoCIII") effective to increase intracellular calcium concentration, in the presence of one or more test compounds, and identifying those test compounds that inhibit an apoCIII-induced increase in intracellular calcium concentration in the pancreatic β cells. In another aspect, the present invention provides methods for treating patients with type I diabetes comprising administering to the patient an amount effective of an inhibitor of apoCIII to reduce apoCIII-induced increase in intracellular calcium concentration in pancreatic β cells.

In a further aspect, the present invention provides methods for diagnosing Type I diabetes or a propensity to develop type I diabetes comprising determining an amount of sialylated apoCIII in a control blood serum sample; and diagnosing those subjects with an elevated amount of sialylated apoCIII in the blood serum sample relative to the control as having type I diabetes, or having a propensity to develop type I diabetes.

In a still further aspect, the present invention provides methods for identifying diabetic patients to be treated with anti-apoCIII therapy, comprising determining an amount of apoCIII patients to be treated with anti-apoCIII therapy, comprising determining an amount of apoCIII in a blood serum sample from a diabetic subject and comparing it to a control blood serum sample; and identifying those subjects with an elevated amount of apoCIII in the blood serum sample relative to the control blood serum sample as being subjects to be treated with anti-apoCIII therapy.

DETAILED DESCRIPTION OF THE INVENTION

Figure 1:
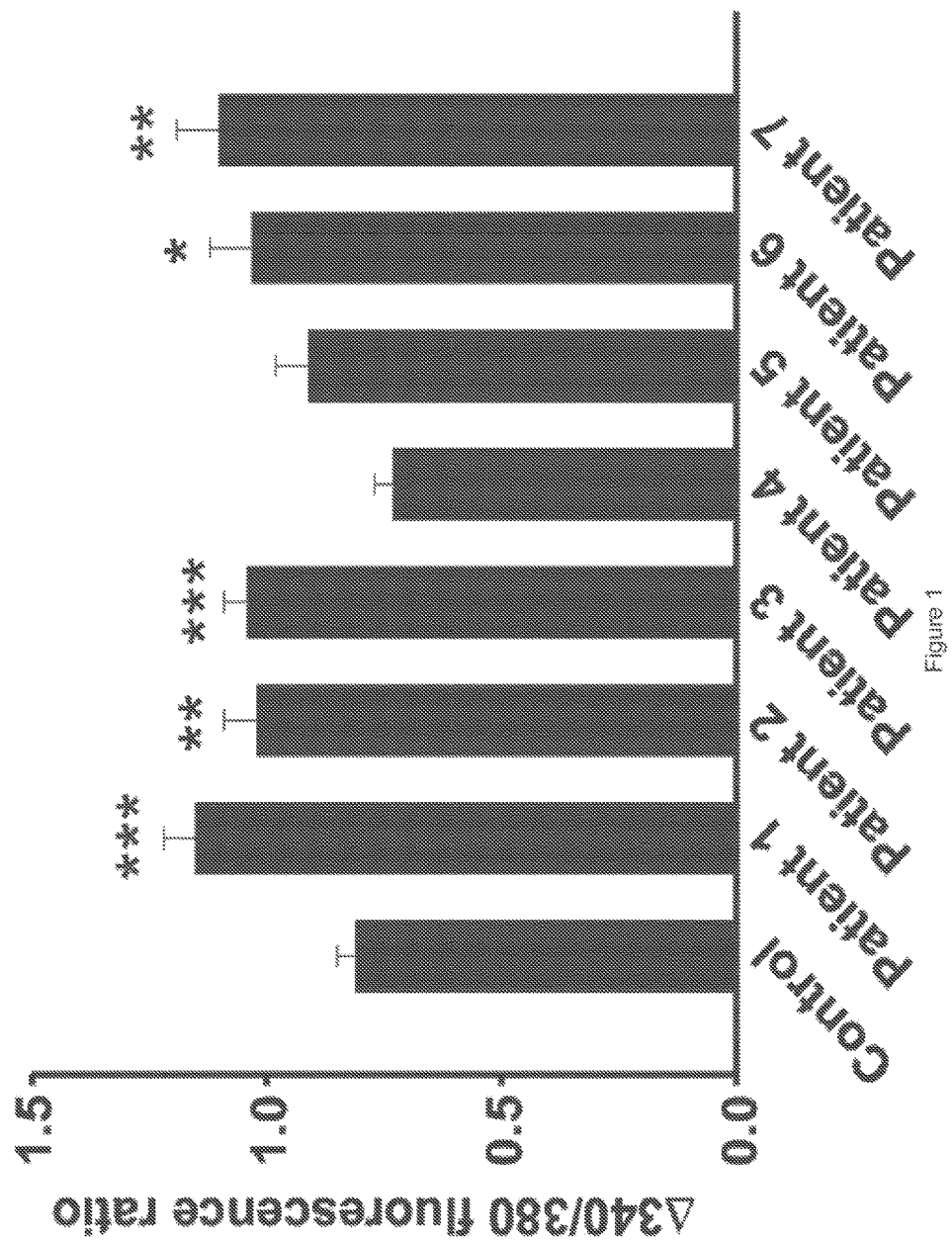
FIG. 1 Changes in $[Ca^{2+}]_i$ in pancreatic β-cells from mice exposed to T1D or control sera. Five out of seven T1D sera induced an enhanced increase in $[Ca^{2+}]_i$, when the cells were depolarized with high concentrations of $K^+$ to open the voltage-gated $Ca^{2+}$-channel, compared to cells that had been exposed to normal serum (n=29, 28, 32, 47, 21, 27, 31 and 18, respectively), \*\*\*P<0.001, \*\*P<0.01 and \*P<0.05 versus control.

Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique*, $2^{nd}$ Ed. (R. I. Freshney. 1987. Liss, Inc. New York, N.Y.), *Gene Transfer and Expression Protocols*, pp. 109-128, ed. E. J. Murray, The Humana Press Inc., Clifton, N.J.), and the Ambion 1998 Catalog (Ambion, Austin, Tex.).

In one aspect, the present invention provides methods of identifying candidate compounds for the treatment of type I diabetes comprising contacting pancreatic β cells with an amount effective of apolipoprotein CIII ("apoCIII") effective to increase intracellular calcium concentration in the presence of one or more test compounds, and identifying those test compounds that inhibit apoCIII-induced increase in intracellular calcium concentration in the pancreatic β cells.

As used herein, "apoCIII" refers to a protein comprising the amino acid sequence shown in SEQ ID NO:2 (Human) (NCBI accession number CAA25233), SEQ ID NO:4 (Rat) (NCBI accession number AA40746), or SEQ ID NO:6 (Macaque) (NCBI accession number CAA48419), (NCBI accession number NP_075603), SEQ ID NO:8 (Mouse) or functional equivalents thereof.

The apoCIII may be substantially purified apoCIII, available, for example, from Sigma Chemical Company (St. Louis, Mo.), wherein "substantially purified" means that it is removed from its normal in vivo cellular environment. Alternatively, the apoCIII may be present in a mixture, such as blood serum from type I diabetic or partially or fully purified therefrom using standard techniques, such as those described below. In a preferred embodiment, substantially purified apoCIII is used.

As discussed below, there are three known isoforms of human apoCIII that have the same amino acid sequence, but which differ in their glycosylation pattern. Thus, in a preferred embodiment, glycosylated apoCIII is used, wherein the glycosylation is preferably sialylation. In an especially preferred embodiments, mono-sialylated or di-sialylated apoCIII is used. Such glycosylated forms may be purchased, for example, from Sigma Chemical Company, or may be partially or fully purified using standard techniques, such as those described below.

As used herein, "pancreatic β cells" are any population of cells that contains pancreatic β islet cells. The cells can be obtained from any mammalian species, or may be present within the mammalian species when the assays are conducted in vivo. Such pancreatic β islet cell populations include the pancreas, isolated pancreatic islets of Langerhans ("pancreatic islets"), isolated pancreatic β islet cells, and insulin secreting cell lines. Methods for pancreatic isolation are well known in the art, and methods for isolating pancreatic islets, can be found, for example, in Cejvan et al., Diabetes 52:1176-1181 (2003); Zambre et al., Biochem. Pharmacol. 57:1159-1164 (1999), and Fagan et al., Surgery 124:254-259 (1998), and references cited therein. Insulin secreting cell lines are available from the American Tissue Culture Collection ("ATCC") (Rockville, Md.). In a further embodiment where pancreatic β cells are used, they are obtained from ob/ob mice, which contain more than 95% β cells in their islets, and are commercially available.

As used herein, "intracellular calcium concentration" refers to cytoplasmic free $Ca^{2+}$ concentration ($[Ca^{2+}]_i$) in the pancreatic β-cell. Such concentrations can be measured by any method known in the art, such as the use of fluorescent calcium indicators, as disclosed herein.

As used herein, "increase intracellular calcium concentration" refers to increasing the concentration during the course of the assay above that seen in the absence of test compounds. The method does not require a specific amount of increase in intracellular calcium concentration over baseline, so long as the compound(s) promotes an increase in intracellular calcium concentration above that seen in the absence of test compounds. In a preferred embodiment, the increase is a statistically significant increase as measured by standard statistical measurements.

The contacting of the pancreatic β cells with the apoCIII may occur before, after, or simultaneously with contacting the cells with one or more test compounds. The contacting can be in vitro, in vivo, or ex vivo.

The present invention further provides compounds identified by the above screening methods, and their use for treating subjects with type I diabetes.

In another embodiment, the methods further comprise synthesizing the test compounds that inhibit apoCIII-induced increase in intracellular calcium concentration in the pancreatic β cells.

When the test compounds comprise polypeptide sequences, such polypeptides may be chemically synthesized or recombinantly expressed. Recombinant expression can be accomplished using standard methods in the art, as disclosed above. Such expression vectors can comprise bacterial or viral expression vectors, and such host cells can be prokaryotic or eukaryotic. Synthetic polypeptides, prepared using the well-known techniques of solid phase, liquid phase, or peptide condensation techniques, or any combination thereof, can include natural and unnatural amino acids. Amino acids used for peptide synthesis may be standard Boc (Nα-amino protected Nα-t-butyloxycarbonyl) amino acid resin with standard deprotecting, neutralization, coupling and wash protocols, or standard base-labile Nα-amino protected 9-fluorenylmethoxycarbonyl (Fmoc) amino acids. Both Fmoc and Boc Nα-amino protected amino acids can be obtained from Sigma, Cambridge Research Biochemical, or other chemical companies familiar to those skilled in the art. In addition, the polypeptides can be synthesized with other Nα-protecting groups that are familiar to those skilled in this art. Solid phase peptide synthesis may be accomplished by techniques familiar to those in the art and provided, such as by using automated synthesizers.

When the test compounds comprise antibodies, such antibodies can be polyclonal or monoclonal. The antibodies can be humanized, fully human, or murine forms of the antibodies. Such antibodies can be made by well-known methods, such as described in Harlow and Lane, Antibodies; A Laboratory Manual, Cold Spring Harbor Laboratory, Cold Spring Harbor, N.Y., (1988). In one example, preimmune serum is collected prior to the first immunization with, for example, apoCIII. A substantially purified apoCIII, or antigenic fragments thereof, together with an appropriate adjuvant, are injected into an animal in an amount and at intervals sufficient to elicit an immune response. Animals are bled at regular intervals, preferably weekly, to determine antibody titer. The animals may or may not receive booster injections following the initial immunization. At about 7 days after each booster immunization, or about weekly after a single immunization, the animals are bled, the serum collected, and aliquots are stored at about −20° C. Polyclonal antibodies against apoCIII can then be purified directly by passing serum collected from the animal through a column to which non-antigen-related proteins prepared from the same expression system without apoCIII bound.

Monoclonal antibodies can be produced by obtaining spleen cells from the animal. (See Kohler and Milstein, Nature 256, 495-497 (1975)). In one example, monoclonal antibodies (mAb) of interest are prepared by immunizing inbred mice with apoCIII, or an antigenic fragment thereof. The mice are immunized by the IP or SC route in an amount and at intervals sufficient to elicit an immune response. The mice receive an initial immunization on day 0 and are rested for about 3 to about 30 weeks. Immunized mice are given one or more booster immunizations of by the intravenous (IV) route. Lymphocytes, from antibody positive mice are obtained by removing spleens from immunized mice by standard procedures known in the art. Hybridoma cells are produced by mixing the splenic lymphocytes with an appropriate fusion partner under conditions which will allow the formation of stable hybridomas. The antibody producing cells and fusion partner cells are fused in polyethylene glycol at concentrations from about 30% to about 50%. Fused hybridoma cells are selected by growth in hypoxanthine, thymidine and aminopterin supplemented Dulbecco's Modified Eagles Medium (DMEM) by procedures known in the art. Supernatant fluids are collected from growth positive wells and are screened for antibody production by an immunoassay such as solid phase immunoradioassay. Hybridoma cells from antibody positive wells are cloned by a technique such as the soft agar technique of MacPherson, Soft Agar Techniques, in Tissue Culture Methods and Applications, Kruse and Paterson, Eds., Academic Press, 1973.

"Humanized antibody" refers to antibodies derived from a non-human antibody, such as a mouse monoclonal antibody. Alternatively, humanized antibodies can be derived from chimeric antibodies that retains or substantially retains the antigen-binding properties of the parental, non-human, antibody but which exhibits diminished immunogenicity as compared to the parental antibody when administered to humans. For example, chimeric antibodies can comprise human and murine antibody fragments, generally human constant and mouse variable regions. Since humanized antibodies are far less immunogenic in humans than the non-human monoclonal antibodies, they are preferred for subsequent therapeutic antibody use.

Humanized antibodies can be prepared using a variety of methods known in the art, including but not limited to (1) grafting complementarity determining regions from a non-human monoclonal antibody onto a human framework and constant region ("humanizing"), and (2) transplanting the non-human monoclonal antibody variable domains, but "cloaking" them with a human-like surface by replacement of surface residues ("veneering"). These methods are disclosed, for example, in, e.g., Jones et al., Nature 321:522-525 (1986); Morrison et al., Proc. Natl. Acad. Sci., U.S.A., 81:6851-6855 (1984); Morrison and Oi, Adv. Immunol., 44:65-92 (1988); Verhoeyer et al., Science 239:1534-1536 (1988); Padlan, Molec. Immun. 28:489-498 (1991); Padlan, Molec. Immunol. 31(3):169-217 (1994); and Kettleborough, C. A. et al., Protein Eng. 4(7):773-83 (1991).

The term antibody as used herein is intended to include antibody fragments thereof which are selectively reactive with apoCIII, or fragments thereof. Antibodies can be fragmented using conventional techniques, and the fragments screened for utility in the same manner as described herein for whole antibodies. For example, $F(ab')_2$ fragments can be generated by treating antibody with pepsin. The resulting $F(ab')_2$ fragment can be treated to reduce disulfide bridges to produce Fab' fragments.

As used herein "selectively reactive" means that the antibodies recognize one or more epitope within apoCIII, but possess little or no detectable reactivity with control proteins, such as bovine serum albumin, under standard conditions such as those disclosed herein.

When the test compounds comprise nucleic acid sequences, such nucleic acids may be chemically synthesized or recombinantly expressed as well. Recombinant expression techniques are well known to those in the art (See, for example, Sambrook, et al., 1989, supra). The nucleic acids may be DNA or RNA, and may be single stranded or double. Similarly, such nucleic acids can be chemically or enzymatically synthesized by manual or automated reactions, using standard techniques in the art. If synthesized chemically or by in vitro enzymatic synthesis, the nucleic acid may be purified prior to introduction into the cell. For example, the nucleic acids can be purified from a mixture by extraction with a solvent or resin, precipitation, electrophoresis, chromatography, or a combination thereof. Alternatively, the nucleic acids may be used with no or a minimum of purification to avoid losses due to sample processing.

When the test compounds comprise compounds other then polypeptides, antibodies, or nucleic acids, such compounds can be made by any of the variety of methods in the art for conducting organic chemical synthesis.

In another aspect, the present invention provides methods for treating patients with type I diabetes comprising administering to the patient an amount effective of an inhibitor of apoCIII to reduce apoCIII-induced increase in intracellular calcium concentration in pancreatic β cells. As used herein, an "inhibitor" of apoCIII includes compounds that reduce the transcription of apoCIII DNA into RNA, compounds that reduce translation of the apoCIII RNA into protein, and compounds that reduce the function of apoCIII protein. Such inhibiting can be complete inhibition or partial inhibition, such that the expression and/or activity of the apoCIII is reduced, resulting in a reduced ability to increase intracellular calcium concentration. Such inhibitors are selected from the group consisting of antibodies that bind to apoCIII; antisense oligonucleotides directed against the apoCIII protein, DNA, or mRNA; small interfering RNAs directed against the apoCIII protein, DNA, or mRNA, and any other chemical or biological compound that can interfere with apoCIII activity. In one embodiment, the inhibitor is identified using the compounds of the present invention. In another embodiment, the inhibitor is selected from the group consisting of (a) apoCIII-selective antibodies, (b) antisense nucleic acid constructs derived from the apoCIII mRNA sequence (SEQ ID NOS: 1, 3, and 5) (NCBI accession numbers X00567 (Human); J02596 (Rat); and X68359 (Macaque), respectively), and (c) small interfering RNA sequences derived from the apoCIII mRNA sequence (SEQ ID NOS: 1, 3, and 5, and 7)) (NCBI accession numbers X00567 (Human); J02596 (Rat); and X68359 (Macaque), and NM_023114 (Mouse) respectively).

Methods for making antibodies against apoCIII or fragments thereof are disclosed above. Antibodies against apoCIII are commercially available (for example, from Academy BioMedical Company (Texas, USA) Chemicon International (California, USA); United States Biological (Massachusetts, USA), Novus Biologicals (Colorado, USA Rockland Immunochemicals (Pennsylvania, USA).

Methods for making antisense oligonucleotides and small interfering RNA sequences against the apoCIII mRNA sequence are well known to those of skill in the art, based on the apoCIII sequences disclosed herein. Antisense oligonucleotides will be complementary to the mRNA expressed from the apoCIII gene, in order to bind to the mRNA to inhibit translation.

In a preferred embodiment for using small interfering RNAs, the RNAs are double stranded RNAs. Methods for using such double stranded RNAs are as described, for example in U.S. Pat. No. 6,506,559. For example, RNA may be synthesized in vivo or in vitro. Endogenous RNA polymerase of the cell may mediate transcription in vivo, or cloned RNA polymerase can be used for transcription in vivo or in vitro. For transcription from a transgene in vivo or an expression construct, a regulatory region (e.g., promoter, enhancer, silencer, splice donor and acceptor, polyadenylation) may be used to transcribe the RNA strand (or strands). The RNA strands may or may not be polyadenylated; the RNA strands may or may not be capable of being translated into a polypeptide by a cell's translational apparatus. RNA may be chemically or enzymatically synthesized by manual or automated reactions. The RNA may be synthesized by a cellular RNA polymerase or a bacteriophage RNA polymerase (e.g., T3, T7, SP6). If synthesized chemically or by in vitro enzymatic synthesis, the RNA may be purified prior to introduction into the cell. For example, RNA can be purified from a mixture by extraction with a solvent or resin, precipitation, electrophoresis, chromatography, or a combination thereof. Alternatively, the RNA may be used with no or a minimum of purification to avoid losses due to sample processing. The RNA may be dried for storage or dissolved in an aqueous solution. The solution may contain buffers or salts to promote annealing, and/or stabilization of the duplex strands.

In another aspect, the present invention also provides pharmaceutical compositions, comprising an inhibitor of apoCIII activity and a pharmaceutically acceptable carrier. In a preferred embodiment, the apoCIII inhibitor is selected from the group consisting of an antibody reactive with apoCIII or a fragment thereof, an antisense oligonucleotide against the apoCIII mRNA sequence, and a small interfering RNA sequence directed against the apoCIII mRNA sequence.

The inhibitors may be admixed with lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol, and tableted or encapsulated for conventional administration. Alternatively, the inhibitors may be dissolved in saline, water, polyethylene glycol, propylene glycol, carboxymethyl cellulose colloidal solutions, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The inhibitor may be made up in a solid form (including granules, powders or suppositories) or in a liquid form (e.g., solutions, suspensions, or emulsions). Inhibitor may be applied in a variety of solutions. Suitable solutions for use in accordance with the invention are sterile, dissolve sufficient amounts of the antibody, and are not harmful for the proposed application. The inhibitor may be subjected to conventional pharmaceutical operations such as sterilization and/or may contain conventional adjuvants, such as preservatives, stabilizers, wetting agents, emulsifiers, buffers etc.

Thus, in a further aspect, the present invention provides a method for diagnosing Type I diabetes or a propensity to develop type I diabetes comprising
  (a) determining an amount of sialylated apoCIII in a blood serum sample from a subject
  (b) comparing an amount of sialylated apoCIII in the blood serum sample from a subject; and
  (c) diagnosing those subjects with an elevated amount of sialylated apoCIII in the blood serum sample relative to the control as having type I diabetes, or having a propensity to develop type I diabetes.

As used herein, the "control blood serum sample" can be any relevant control that provides a suitable standard against which to compare the amount of sialylated apoCIII in the subject's serum sample, including but not limited to blood serum samples from a non-diabetic subject; previous blood serum samples from the subject being tested, and known reference standards.

As disclosed herein, the inventor has discovered that the sialylated forms of apoCIII predominate in type I diabetic patients, and that analyzing the levels of sialylated apoCIII in blood serum relative to control will provide a better read out for diagnosis of patients with type I diabetes or a propensity to develop type I diabetes than analyzing apoCIII levels as a whole.

In a further embodiment, the level of mono-sialylated apoCIII in the subject relative to control is analyzed; in another embodiment, the level of di-sialylated apoCIII in the subject relative to control is analyzed; and in a further embodiment, both measurements are made.

The method does not require a specific amount of increase in sialylated apoCIII in the blood serum sample over control, although it is preferred that the increase is a statistically significant increase as measured by standard statistical measurements.

The diagnostic methods of the invention can be used in combination with any other diagnostic methods known in the art, in order to increase the accuracy of the assays.

In a further aspect, the present invention provides methods for identifying diabetic patients to be treated with anti-apoCIII therapy, comprising
  (a) Determining an amount of apoCIII in a blood serum sample from a diabetic subject and comparing it to a control blood serum sample; and
  (b) Identifying those subjects with an elevated amount of apoCIII in the blood serum sample relative to the control blood serum sample as being subjects to be treated with anti-apoCIII therapy.

As used herein, the "control blood serum sample" can be any relevant control that provides a suitable standard against which to compare the amount of apoCIII in the subject's serum sample, including but not limited to blood serum samples from diabetic subjects that do not benefit or have not benefited from anti-apoCIII therapy, previous blood serum samples from the subject being tested, and known reference standards.

In an embodiment of this aspect of the invention, the method further comprises treating those subjects identified as subjects to be treated with anti-apoCIII therapy with anti-apoCIII therapeutic compounds. Such compounds include, but are not limited to, test compounds identified by the methods of the invention as inhibiting the apoCIII-induced increase in intracellular calcium concentration in pancreatic β cells; apoCIII antibodies; and antisense nucleic acids and small interfering RNAs that selectively bind to apoCIII mRNA as disclosed herein.

In this aspect, the methods of the invention provide a means to identify the patient population that will most benefit from anti-apoCIII therapy, and thus to minimize use of the therapeutic methods on those patients that will not benefit. Such patients can be any patient population that will benefit from anti-apoCIII therapy, preferably diabetic patients (type I or II), and most preferably type I diabetic patients.

According to this aspect of the invention, the amount of apoCIII can be of total apoCIII, or, preferably, of sialylated apoCIII. In further embodiments, the level of mono-sialylated apoCIII in the subject relative to control is analyzed; in another embodiment, the level of di-sialylated apoCIII in the subject relative to control is analyzed; and in a further embodiment, both measurements are made.

The method does not require a specific amount of increase in apoCIII in the blood serum sample over control, although it is preferred that the increase is a statistically significant increase as measured by standard statistical measurements.

EXAMPLES

Materials and Methods

Media The basal medium used both for isolation of cells and for experiments was a HEPES buffer (pH 7.4), containing (in mM): 125 NaCl, 5.9 KCl, 1.3 CaCl$_2$, 1.2 MgCl$_2$, 25 HEPES. Bovine serum albumin was added to the medium at a concentration of 1 mg/ml. For cell culture, RPMI 1640 medium was supplemented with 100 µg/ml streptomycin, 100 IU penicillin and 10% fetal calf-, normal human- or diabetic serum.

Preparation of Cells Adult mice from a local colony (3) were starved overnight. Pancreatic islets were isolated by a collagenase technique and cell suspensions were prepared as previously described (4, 5). Cells were seeded onto glass coverslips and cultured at 37° C. in a humidified atmosphere of 5% CO$_2$ in air.

Preparation and Purification of Sera: Sera from T1D patients and control subjects were collected, identically sterile-processed and stored frozen at −20° C. until used. The sera were heat-inactivated by incubation at 56° C. for 30 min. Thereafter β-cells were incubated overnight in RPMI 1640 culture medium with 10% of the sera and changes in $[Ca^{2+}]_i$ were recorded, subsequent to depolarization with 25 mM KCl. The five T1D sera that induced an enhanced $[Ca^{2+}]_i$ response were centrifuged and the supernatant was passed through a 0.45 mm sterile filter. Samples were loaded on Sep-Pak C$_{18}$ (Waters, Ma) preconditioned with 0.1% TFA. After a wash with 0.1% TFA, proteins were eluted with 60% acetonitrile in 0.1% TFA and thereafter lyophilized. Batches of one milligram of the lyophilized sample were dissolved in 500 µl 0.1% TFA, centrifuged and injected into a RP-HPLC with a Vydac C$_{18}$ (0.46×25 cm) column (Grace Vydac, Hesperia, Ca). The separation was made using a linear gradient of 20-60% acetonitrile in 0.1% TFA for 40 min at 1 ml/min. Fractions of 1 ml were collected and lyophilized.

Purification of Isoforms of Apolipoprotein CIII (apoCIII) ApoCIII was purified from human serum by adsorption to a lipid emulsion and delipidation, followed by chromatography of the lipid-associated proteins under denaturing conditions in guanidinium chloride and urea, respectively, as previously described (6). The apoCIII isoforms were dialyzed against ammonium bicarbonate and lyophilized before use.

Measurements of $[Ca^{2+}]_i$ Cells, attached to coverslips, were pretreated with the different compounds as described in the results and thereafter incubated in basal medium with 2 µM fura-2AM (Molecular Probes, Eugene, Oreg.) for 30 min. The coverslips were mounted as the bottom of an open chamber and cells were perfused with medium. Fluorescence signals were recorded with a SPEX Fluorolog-2 system connected to an inverted Zeiss Axiovert epifluorescence microscope. The excitation and emission wavelengths were 340/380 and 510 nm, respectively. The results are presented as 340/380 excitation ratios, directly representative of $[Ca^{2+}]_i$ (7).

Patch Clamp Whole-cell $Ca^{2+}$ currents were recorded by using the perforated-patch variant of the whole-cell patch-clamp recording technique to eliminate the loss of soluble cytoplasmic components. Electrodes were filled with (in mM): 76 Cs$_2$SO$_4$, 1 MgCl$_2$, 10 KCl, 10 NaCl, and 5 HEPES (pH 7.35), as well as amphotericin B (0.24 mg/ml) to permeabilize the cell membrane and allow low-resistance electrical access without breaking the patch. Pancreatic β-cells were incubated in RPMI 1640 medium with apoCIII (10:g/ml) or vehicle overnight. The cells were bathed in a solution containing (in mM): 138 NaCl, 10 tetraethylammonium chloride, 10 CaCl$_2$, 5.6 KCl, 1.2 MgCl$_2$, 5 HEPES and 3 D-glucose (pH 7.4). Whole-cell currents induced by voltage pulses (from a holding potential of −70 mV to several clamping potentials from −60 to 50 mV in 10 mV increments, 100 ms, 0.5 Hz) were filtered at 1 kHz and recorded. All recordings were made with an Axopatch 200 amplifier (Axon Instruments, Foster City, Calif.) at room temperature (about 22° C.). Acquisition and analysis of data were done using the software program pCLAMP6 (Axon Instruments, Foster City, Calif.).

Protein Characterization Primary sequence was obtained in ABI 494C and cLC sequencers. Protein molecular weights were determined by electrospray mass spectrometry (AutoSpec hybrid tandem mass spectrometer, Micromass). For recording of positive-ion conventional-ES spectra, samples (16 pmol/ml) were introduced into the ES interface by infusion or loop injection at a flow rate of 3 ml/min. To determine the position of the glycosylation, the native protein was digested with trypsin 1:10 w/w (Promega, Madison, Wis.). The resulting fragments were separated by HPLC using a Vydac C$_8$ (2.1×150 mm) and a gradient of 0-50% B in 50 min (buffer A, 5% acetonitrile/0.1% TFA; B, 80% acetonitrile/0.1% TFA). The fragments separated were applied to mass analysis.

Quantification of apoCIII Sera were collected and prepared as described above. The relative amounts of apoCIII in T1D serum and control serum, respectively were evaluated by comparisons of the peak area corresponding to apoCIII in the second RP-HPLC.

Flow Cytometric Analysis of Cell Death RINm5F cells were cultured for 36 h in the presence of 10% control serum, control serum and 40 µg/ml apoCIII or T1D serum with or without 100 or 200 µg/ml anti-apoCIII. The whole cell population was collected and stained with EGFP-conjugated Annexin V and propidium iodide (PI) (BD PharMingen) and analyzed on a FACscan using CELL-Quest acquisition software (Becton Dickinson, Immunocytometry System). FACS gating, based on forward and side scatter, was used to exclude cellular debris and autofluorescence and typically 10 000 cells were selected for analysis.

Statistical Analysis Statistical significance was evaluated by Student's t-test and P values<0.05 were considered significant. Data are expressed as means±SEM.

Results and Discussion

ApoCIII plays a key role in the regulation of the metabolism of triglyceride-rich lipoprotein (TRL) (8). It controls the catabolism of TRL by inhibiting the activity of lipoproteinlipase (LPL) (9, 10), thereby inducing hypertriglyceridemia. ApoCIII also inhibits the binding of remnant lipoproteins to catabolic receptors like the LDL receptor related protein (LRP) (11). When the apoCIII gene was disrupted in knock-out mice, there was a 70% reduction in triglyceride levels (12). Overexpression of human apoCIII in transgenic mice results in hypertriglyceridemia (13). ApoCIII is a 79-residue, 8.8 kDa polypeptide (14) with three known isoforms that differ in the extent of glycosylation, $CIII_0$ (no sialic acid), $CIII_1$ (one sialic acid residue), $CIII_2$ (two sialic acid residues), contributing approximately 10%, 55% and 35%, respectively, of total plasma apoCIII (15). Mutagenesis of the glycosylation site and expression in stable cell lines suggest that intracellular glycosylation is not required for the transport and secretion functions (16). Lack of glycosylation does not affect the affinity of apoCIII for VLDL and HDL (16). Insulin is involved in the regulation of the apoCIII gene and induces a dose-dependent down-regulation of the transcriptional activity. Overexpression of the apoCIII gene could contribute to the hypertriglyceridemia seen in T1D patients (17). However, mice transgenic for the human apoCIII gene are neither insulin-resistant nor hyperinsulinemic (18). The concentration of apoCIII has previously been found to be higher in diabetic patients than in normal subjects (19-27). In insulin deficient rats there was no significant change in apoCIII in one study (28), while others have reported an increase in the proportions of the sialylated apoCIII (29, 30).

Figure 2:
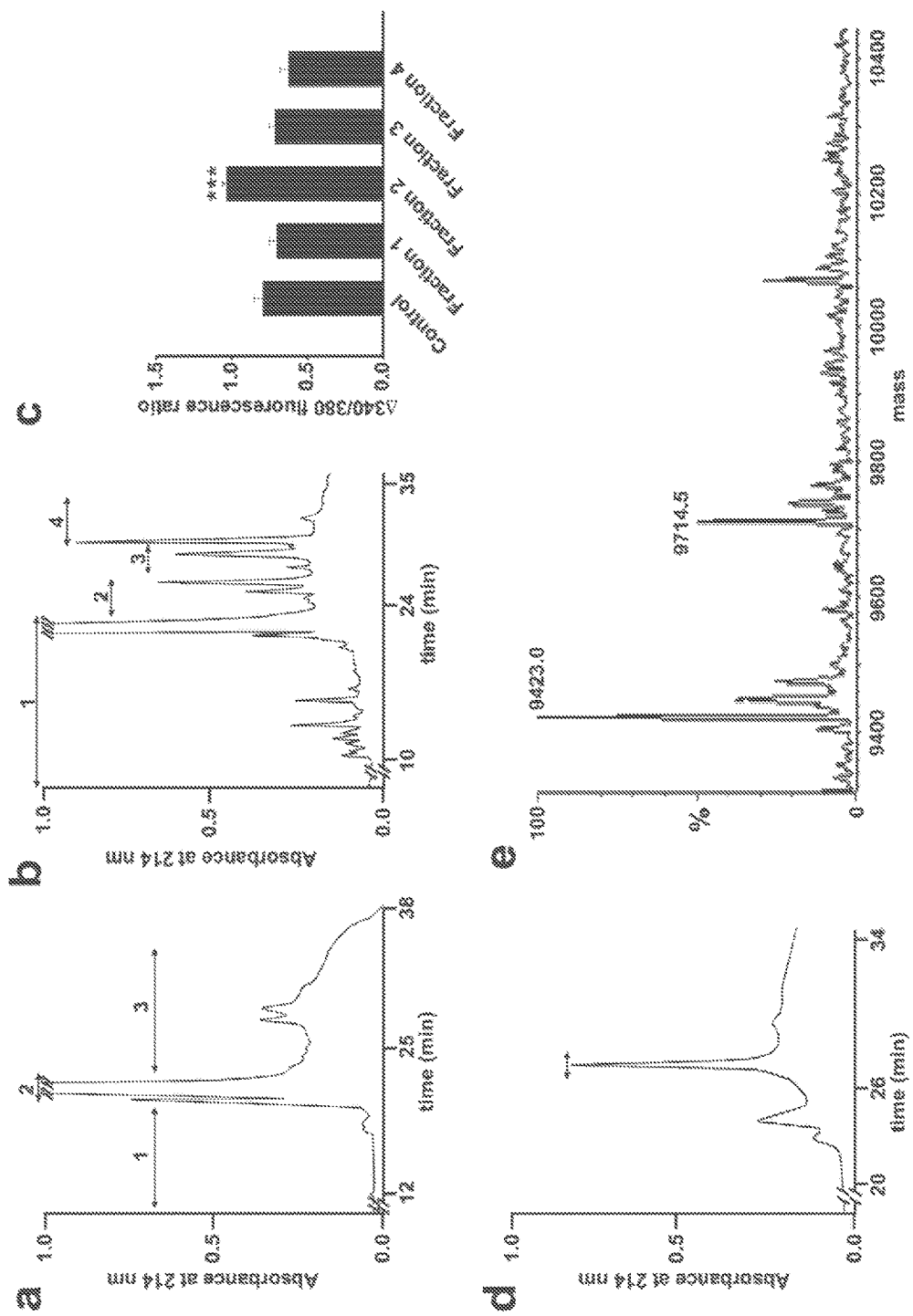
FIG. 2 Stepwise separation and identification of the active fraction in T1D serum. A, After the first RP-HPLC separation the fraction marked 3 was found to give a higher increase in $[Ca^{2+}]_i$. B, Fraction 3 (FIG. 2A) was rerun on RP-HPLC under identical conditions. The fractions were again tested for $[Ca^{2+}]_i$ stimulating activity (FIG. 2C), and one positive fraction (No. 2) was identified. D, The active fraction (FIG. 2B) was re-chromatographed. The fraction, inducing a higher increase in $[Ca^{2+}]_i$ when β-cells were depolarized with high concentrations of $K^+$, is marked with a bar. C, Pancreatic β-cells incubated with four fractions from RP-HPLC of diabetic sera from FIG. 2B (n=6, 11, 12, 11 and 10, respectively), \*\*\*P<0.001 versus control. E, The active fraction from FIG. 2C was analyzed by electrospray mass spectrometry.

We have tested sera from seven newly diagnosed T1D patients (Table 1). Mouse pancreatic β-cells were cultured overnight with 10% sera from patients or normal subjects. Sera from five of the patients induced a significantly higher increase in $[Ca^{2+}]_i$, when cells were depolarized with 25 mM KCl, leading to an opening of voltage-gated L-type $Ca^{2+}$-channels, than sera from healthy blood donors (FIG. 1). Positive sera were pooled, concentrated and fractionated by reversed phase (RP)-HPLC. When fractions were tested on isolated mouse pancreatic β-cells, one fraction (No. 3, FIG. 2A) eluting between 52-60% acetonitrile, induced a more pronounced increase in $[Ca^{2+}]_i$ when cells were depolarized with high concentrations of $K^+$. After further purification of the component(s) in this fraction by repeated RP-HPLC runs (FIG. 2B,D), all fractions obtained were tested for effects on $[Ca^{2+}]_i$ by incubation with mouse β-cells overnight. The results from this second purification (FIG. 2B) showed a higher activity in fraction 2 (FIG. 2C). The protein that induced an increase in $[Ca^{2+}]_i$ indicated by the bar in FIG. 2D was determined. Sequence information was obtained both by C-terminal and N-terminal degradations. The sequences were identical to those of human apoCIII for 20 N-terminal and 5 C-terminal residues.

TABLE 1

Characterization of the T1D patients.

| Patient | Sex | Age (years) | Duration of T1D (weeks) | Medication | ICA | GAD | IA-2 |
|---|---|---|---|---|---|---|---|
| 1 | M | 32 | <1 | No* | Pos | Pos | Pos |
| 2 | F | 32 | 12 | No* | Neg | Pos | Neg |
| 3 | F | 31 | <1 | No* | Pos | Pos | Pos |
| 4 | F | 23 | <1 | No* | Pos | Neg | ND |
| 5 | M | 19 | <1 | No* | Neg | Neg | Pos |
| 6 | F | 35 | <1 | No* | Pos | Pos | Pos |
| 7 | F | 33 | 28 | No* | Pos | Pos | ND |

Gender of the patients is designated as F, female, and M, male.
The presence (Pos), absence (Neg) or no data available (ND) of antibodies to islet cells (ICA), GAD and tyrosine phosphatase IA2 (IA-2) are marked in the table.
Healthy blood donors, all negative for ICA, GAD and IA-2, served as sources of control sera.
*Insulin was the only medication administered.

Figure 3:
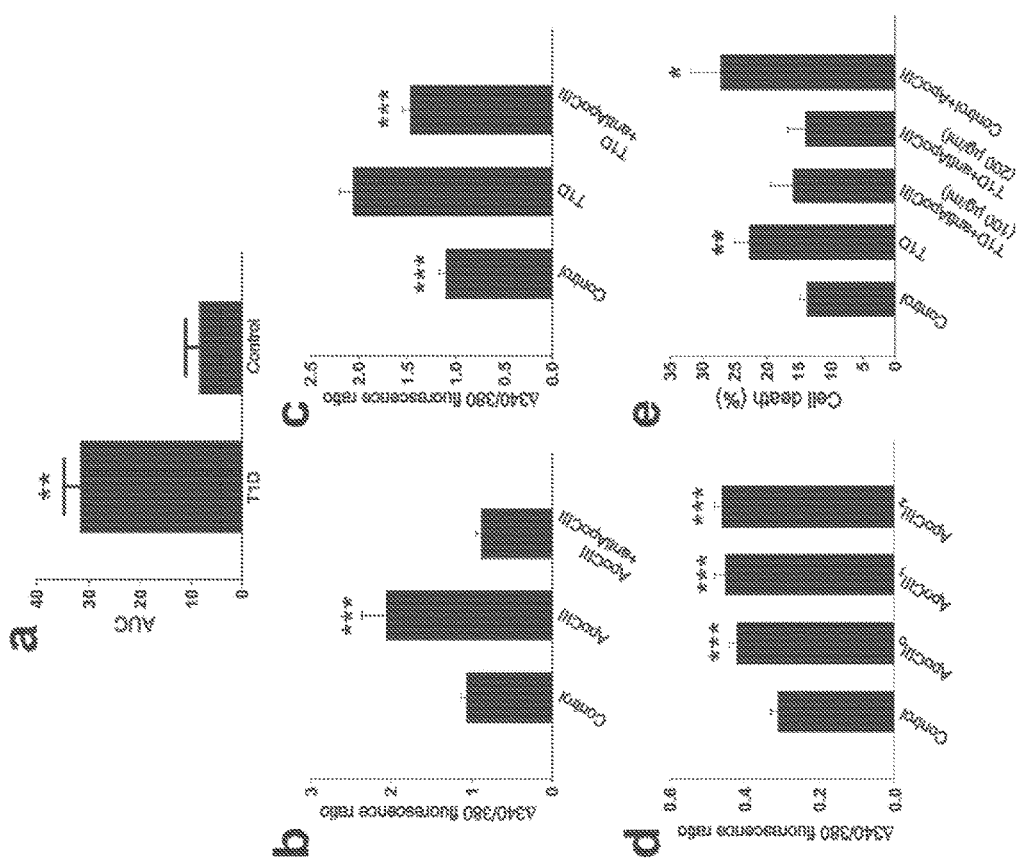
FIG. 3 Amounts of apoCIII in T1D serum and effects on $[Ca^{2+}]_i$ and cell death. A, Relative levels of $apoCIII_{1+2}$ in T1D and control serum, given as area under the curve (AUC), \*\*P<0.01 (n=5). B, Pancreatic β-cells were incubated with apoCIII or apoCIII+antibodies against human apoCIII (n=63, 35 and 33), \*\*\*P<0.001 versus control. C, β-cells were incubated with a control or a T1D serum and T1D serum+anti-apoCIII (n=18, 17 and 20), \*\*\*P<0.001 versus T1D serum. D, Mouse β-cells were incubated with $apoCIII_0$, $apoCIII_1$, $apoCIII_2$ or the vehicle (control) (n=54, 40, 48, 37), \*\*\*P<0.001 versus control. E, The insulin secreting cell line RINm5F was exposed to control and T1D sera and T1D serum with the addition of two concentrations of anti-apoCIII and finally control serum with apoCIII (n=5), \*P<0.05 and \*\*P<0.01, versus control.

We analyzed the apoCIII purified from T1D sera by mass spectrometry for subcomponent identification. The major components had apparent masses of 9423 and 9714 Da (FIG. 2E), corresponding to the mono- and di-glycosylated forms of apoCIII (theoretical, calculated values are: $CIII_0$ 8764 Da, $CIII_1$ 9420 Da, $CIII_2$ 9712 Da). To determine the positions of glycosylation, the protein was digested with trypsin and the fragments were separated by RP-HPLC. When the separated fragments were analyzed by mass spectrometry, seven of the eight fragments showed masses identical to the theoretical values. The mass difference was localized to the C-terminal fragment, previously shown to be glycosylated (31). The absence of a non-glycosylated C-terminal fragment indicated that the isolated apoCIII forms were glycosylated. The relative amounts of apoCIII in T1D and control sera were evaluated by comparisons of the peak area corresponding to apoCIII in the second RP-HPLC (FIG. 3A). In T1D sera the levels of the sialylated isoforms of apoCIII ($apoCIII_1$ and $apoCIII_2$) were four-fold higher than in non-diabetic sera. The non-sialylated isoform ($apoCIII_0$) could not be detected.

The concentration of apoCIII has been reported to be between 6-14 mg/dl in control subjects and 9-27 mg/dl in diabetics (19, 20, 24-27). These variations may to a certain extent reflect the fact that various methods have been used for the determinations. In our experiments we have used 10% T1D serum in the culture medium instead of 10% fetal calf serum normally used, and therefore we chose to use concentrations in the range 10-50 μg/ml. We have tested concentrations from 1-50 μg/ml and with 1, 3 and 6 μg/ml we did not see any effects, but with the concentrations 10-50 μg/ml we had responses.

Commercially available apoCIII (Sigma), which constitutes a mixture of $apoCIII_1$ and $apoCIII_2$, was tested at a concentration of 10 μg/ml and was shown to stimulate $Ca^{2+}$ influx as the product isolated from T1D sera (FIG. 3B). Co-incubation of β-cells with 100 μg/ml of a polyclonal antibody against human apoCIII (Academy BioMedical Company, Houston, Tex.) blocked the activity of both the commercial apoCIII and the T1D serum (FIG. 3B,C). The polyclonal antibody had no activity by itself (data not shown). When testing the three isoforms of apoCIII by incubation of β-cells at a concentration of 10 μg/ml, both the glycosylated ($CIII_1$ and $CIII_2$) and the un-glycosylated isoform caused significantly higher increase in $[Ca^{2+}]_i$ than cells that had been incubated with only the vehicle, 0.1% triflouroacetic acid (TFA) (FIG. 3D). To study the effect of possible binding of apoCIII to serum lipoproteins in the culture medium, cells were incubated in basal buffer containing no serum and 10 μg/ml $apoCIII_1$ for 2 and 6 h. There was a significantly elevated increase in $[Ca^{2+}]_i$ upon depolarization in all the experiments where the cells had been exposed to apoCIII$_1$ for 6 h, but only in one out of three experiments where the incubation time was only 2 h (data not shown).

There was a higher percentage of dead cells in the cell population exposed to T1D serum. This effect was prevented by the addition of anti-apoCIII (FIG. 3E). Furthermore, the addition of pure apoCIII to culture medium with control serum resulted in an increased cell death.

Figure 4:
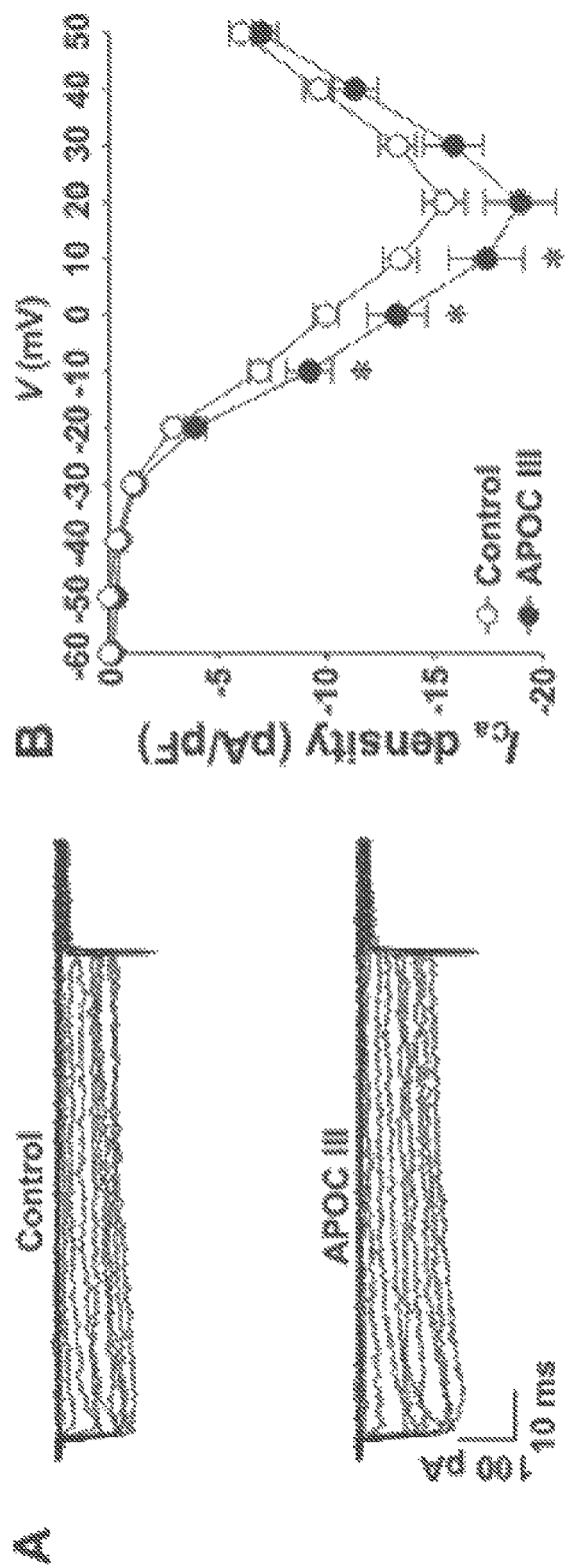
FIG. 4 Interaction of apoCIII with the voltage-gated L-type $Ca^{2+}$ channel. A, Summary graph of current density-voltage relationships. ApoCIII-treated cells (filled circles, n=56) and control cells (open circles, n=55) were depolarized to potentials between −60 and 50 mV, in 10 mV increments, from a holding potential of −70 mV, \*P<0.05. B, Sample whole-cell $Ca^{2+}$ current traces from a control cell (cell capacitance: 4.3 pF) and a cell incubated with apoCIII (cell capacitance: 4.2 pF). Cells were depolarized by a set of voltage pulses (100 ms, 0.5 Hz) between −60 and 50 mV, in 10 mV increments, from a holding potential of −70 mV.

To elucidate the molecular mechanism underlying the stimulatory effect of apoCIII on $[Ca^{2+}]_i$, the activity of voltage-gated $Ca^{2+}$-channels was analyzed in β-cells incubated with 10 µg/ml apoCIII. ApoCIII-treated cells displayed larger $Ca^{2+}$-channel currents than control cells during depolarizations in the range −10 to 10 mV, from a holding potential of −70 mV (FIG. 4A,B). These data demonstrate that apoCIII modulated the activity of the voltage-gated L-type $Ca^{2+}$-channel and that the effect occurred in the range of physiological depolarizations. So far immunoblot experiments have not revealed a direct interaction of apoCIII with the $Ca^{2+}$-channel (data not shown). Future experiment will clarify to what extent this reflects imperfectness in the immunoprecipitation protocol or the actual true situation.

Our study shows that the sialylated forms of apoCIII were on average four-fold higher in sera from newly diagnosed T1D patients than in sera from healthy subjects. ApoCIII induced both an increase in $[Ca^{2+}]_i$ and β-cell death. The molecular mechanism underlying the stimulatory effect of apoCIII on $[Ca^{2+}]_i$ reflected an activation of the voltage-gated L-type $Ca^{2+}$-channel. Addition of an antibody against apoCIII blocked the effects of both T1D serum and apoCIII on $[Ca^{2+}]_i$ as well as on β-cell death. This suggests that the $Ca^{2+}$ dependent cytotoxic effect of T1D serum on the pancreatic β-cell is mediated by apoCIII.

REFERENCES CITED

1. Efendic, S., Kindmark, H. & Berggren, P. O. (1991) *J Intern Med Suppl* 735, 9-22.
2. Juntti-Berggren, L., Larsson, O., Rorsman, P., Ammala, C., Bokvist, K., Wahlander, K., Nicotera, P., Dypbukt, J., Orrenius, S., Hallberg, A. & Berggren, P. O. (1993) *Science* 261, 86-90.
3. Hellman, B. (1965) *Ann NY Acad Sci* 131, 541-58.
4. Nilsson, T., Arkhammar, P., Hallberg, A., Hellman, B. & Berggren, P. O. (1987) *Biochem J* 248, 329-36.
5. Lernmark, A. (1974) *Diabetologia* 10, 431-8.
6. Bengtsson-Olivecrona, G. & Olivecrona, T. (1991) *Methods Enzymol* 197, 345-56.
7. Kindmark, H., Kohler, M., Efendic, S., Rorsman, P., Larsson, O. & Berggren, P. O. (1992) *FEBS Lett* 303, 85-90.
8. Fredenrich, A. (1998) *Diabetes Metab* 24, 490-5.
9. Krauss, R. M., Herbert, P. N., Levy, R. I. & Fredrickson, D. S. (1973) *Circ Res* 33, 403-11.
10. Ginsberg, H. N., Le, N. A., Goldberg, I. J., Gibson, J. C., Rubinstein, A., Wang-Iverson, P., Norum, R. & Brown, W. V. (1986) *J Clin Invest* 78, 1287-95.
11. Kowal, R. C., Herz, J., Weisgraber, K. H., Mahley, R. W., Brown, M. S. & Goldstein, J. L. (1990) *J Biol Chem* 265, 10771-9.
12. Maeda, N., Li, H., Lee, D., Oliver, P., Quarfordt, S. H. & Osada, J. (1994) *J Biol Chem* 269, 23610-6.
13. Ito, Y., Azrolan, N., O'Connell, A., Walsh, A. & Breslow, J. L. (1990) *Science* 249, 790-3.
14. Brewer, H. B., Jr., Shulman, R., Herbert, P., Ronan, R. & Wehrly, K. (1974) *J Biol Chem* 249, 4975-84.
15. Kashyap, M. L., Srivastava, L. S., Hynd, B. A., Gartside, P. S. & Perisutti, G. (1981) *J Lipid Res* 22, 800-10.
16. Roghani, A. & Zannis, V. I. (1988) *J Biol Chem* 263, 17925-32.
17. Chen, M., Breslow, J. L., Li, W. & Leff, T. (1994) *J Lipid Res* 35, 1918-24.
18. Reaven, G. M., Mondon, C. E., Chen, Y. D. & Breslow, J. L. (1994) *J Lipid Res* 35, 820-4.
19. Briones, E. R., Mao, S. J., Palumbo, P. J., O'Fallon, W. M., Chenoweth, W. & Kottke, B. A. (1984) *Metabolism* 33, 42-9.
20. Joven, J., Vilella, E., Costa, B., Turner, P. R., Richart, C. & Masana, L. (1989) *Clin Chem* 35, 813-6.
21. Stewart, M. W., Laker, M. F. & Alberti, K. G. (1994) *J Intern Med Suppl* 736, 41-6.
22. Bren, N. D., Rastogi, A. & Kottke, B. A. (1993) *Mayo Clin Proc* 68, 657-64.
23. Nestel, P. J. & Fidge, N. H. (1982) *Adv Lipid Res* 19, 55-83.
24. Blackett, P., Sarale, D. C., Fesmire, J., Harmon, J., Weech, P. & Alaupovic, P. (1988) *South Med J* 81, 469-73.
25. al Muhtaseb, N., al Yousuf, A. & Bajaj, J. S. (1992) *Pediatrics* 89, 936-41.
26. Manzato, E., Zambon, A., Lapolla, A., Zambon, S., Braghetto, L., Crepaldi, G. & Fedele, D. (1993) *Diabetes Care* 16, 469-75.
27. Reverter, J. L., Senti, M., Rubies-Prat, J., Lucas, A., Salinas, I., Pizarro, E., Pedro-Botet, J. & Sanmarti, A. (1993) *Clin Chim Acta* 223, 113-20.
28. O'Looney, P., Irwin, D., Briscoe, P. & Vahouny, G. V. (1985) *J Biol Chem* 260, 428-32.
29. Callow, M. J. & Redgrave, T. G. (1993) *Biochim Biophys Acta* 1168, 271-9.
30. Bar-On, H., Roheim, P. S. & Eder, H. A. (1976) *J Clin Invest* 57, 714-21.
31. Ito, Y., Breslow, J. L. & Chait, B. T. (1989) *J Lipid Res* 30, 1781-7.

I claim:

1. A method for treating diabetes, comprising administering to a diabetic subject an amount effective of an apoCIII inhibitor to treat the diabetes.

2. The method of claim 1, wherein the apoCIII inhibitor is selected from the group consisting of an apoCIII-selective antibody, an antisense oligonucleotide directed against the apoCIII mRNA, and a small interfering RNA directed against the apoCIII mRNA.

3. The method of claim 2 wherein the apoCIII inhibitor comprises an apoCIII-selective antibody.

4. The method of claim 2 wherein the apoCIII inhibitor comprises an antisense oligonucleotide directed against the apoCIII mRNA.

5. The method of claim 2 wherein the apoCIII inhibitor comprises a small interfering RNA directed against the apoCIII mRNA.

* * * * *